United States Patent [19]

Grossman

[11] 4,382,781
[45] May 10, 1983

[54] DENTAL APPLIANCE

[76] Inventor: Richard C. Grossman, 211 Spalding Dr., #107 - South, Beverly Hills, Calif. 90212

[21] Appl. No.: 310,495

[22] Filed: Oct. 13, 1981

[51] Int. Cl.³ ............................................... A01C 7/00
[52] U.S. Cl. ..................................................... 433/17
[58] Field of Search ...................... 433/5, 6, 7, 17, 18; 29/517; 174/13

[56] References Cited

U.S. PATENT DOCUMENTS 3,119,182  1/1964  Miller et al. ........................... 433/17
3,988,831  11/1976  Wallshein ............................... 433/17

Primary Examiner—Robert Peshock
Attorney, Agent, or Firm—Charles H. Schwartz; Ellsworth R. Roston

[57] ABSTRACT

A dental appliance for use with a variety of different sizes and shapes of elongated wire-like members including: a metal tubular member for attachment to a band which band encircles a tooth for support and with the metal tubular member forming an open passage extending from one end of the tubular member to the other end of the tubular member. The open passage has a greater height than width and with the passage large enough to receive different sizes and shapes of wire-like members. An insert member has a size in one direction approximately the same as the width of the open passage and having a size in the other direction substantially equal to one-half of the height of the open passage so that two inserts substantially fill the open passage. Each insert also forms an elongated passage having a cross-section smaller in size than one-half of the cross-section of the open passage through the tubular member, thereby providing for a variety of different size passages through the combination of the tubular member and one or two of the inserts within the tubular member.

14 Claims, 17 Drawing Figures

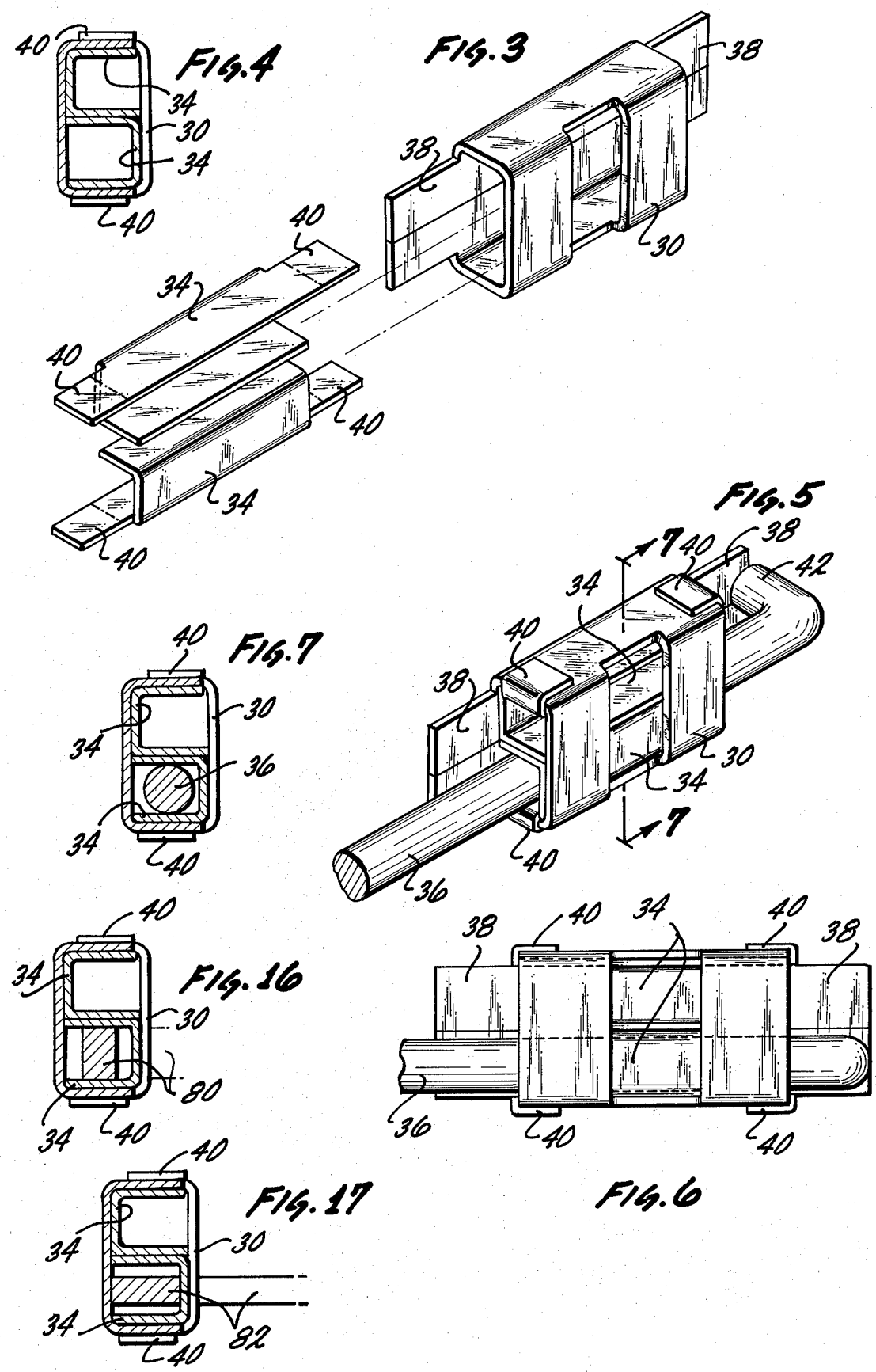

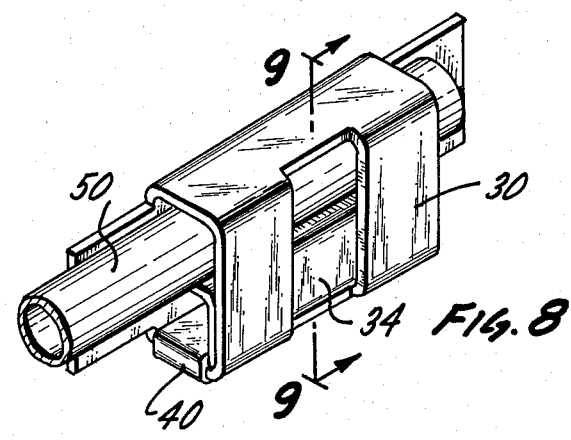
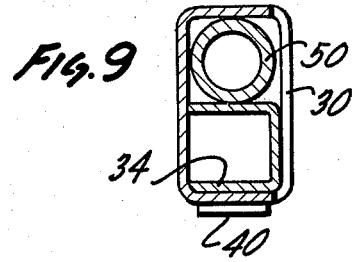
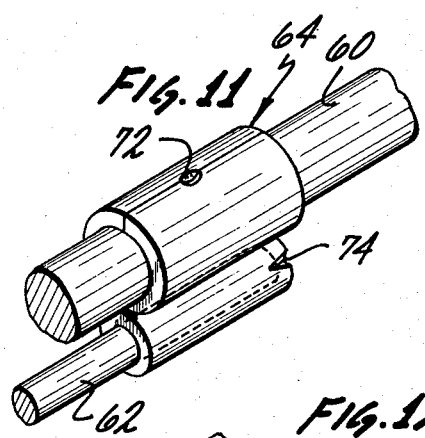
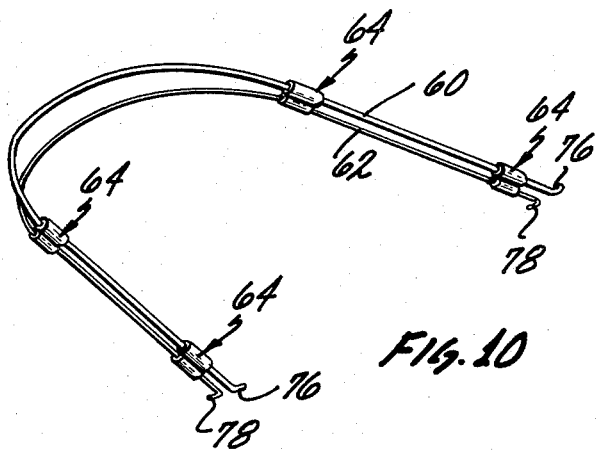
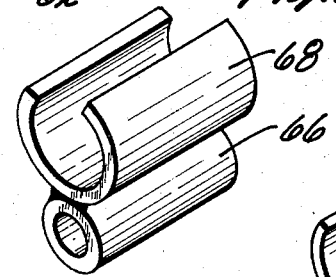
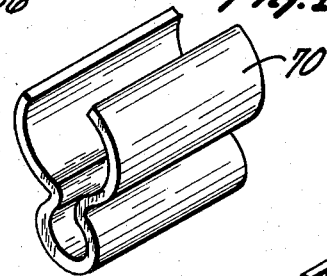
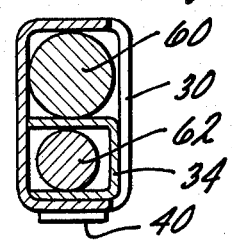

DENTAL APPLIANCE

BACKGROUND OF THE INVENTION

1. Field of the Invention

The present invention is directed to a dental appliance for supporting orthodontic braces such as elongated wire-like members for correcting irregularities of the teeth.

2. Description of the Prior Art

Prior art dental appliances have been used to support orthodontic braces to produce corrections in the irregularities of the teeth. The devices to provide for the correction of the irregularities may take different forms and may provide for various individual teeth being adjusted in position to produce a proper visual appearance and bite.

In general, the prior art devices rely on the elongated wire-like members being positioned on the buccal or cheek side of the teeth so as to produce the proper pressures and forces to adjust individually the positions of the teeth. In the prior art, numerous types of buccal appliances have been used for attachment to molars so as to support various types of elongated tubes and wires to produce the proper pressure and force on the individual teeth to provide for the individual positioning. These types of buccal appliances and specifically the resultant braces are visible since they are on the outside of the teeth and are thereby unsightly. In addition, the buccal appliances and braces may be uncomfortable since they are mounted on the outside of the teeth.

It has been proposed to locate the braces on the lingual or tongue side of the teeth so as to provide for the individual repositioning of the teeth by adhesively affixing bracket members to individual ones of the teeth and with the individual bracket members receiving the tubes or wires to provide for the proper pressure and forces.

SUMMARY OF THE INVENTION

The present invention provides for a dental appliance to allow for completely hidden braces located on the lingual side of the teeth. Specifically, the dental appliance of the present invention allows for the use of a variety of different sizes and shapes of elongated wires or tubes and provides for very versatile and complete flexibility in the application of the braces to the teeth. In particular, the dental appliance of the present invention uses a lingual sheath insert and with one or more such inserts positioned within a metal tubular member. The tubular member is attached to a band and the band extends around a molar so as to locate the dental appliance on the lingual side of the molar. Various combinations and numbers of the sheath insert are located within the metal tubular member to provide for the dental appliance of the present invention accommodating either a tubular member or a wire member and with the tubular and wire members having different sizes or different shapes in accordance with the desired use of the orthodontic appliance.

The present invention also includes a separate double clip member which may be used with the dental appliance of the present invention and with the clip used to accommodate both a smaller and larger size wire and with the clip maintaining the different size wires in a particular spaced relationship.

The dental appliance of the present invention, when used in combination with other devices, allows for the orthodontics to be accomplished using completely hidden structures providing the appropriate pressures and forces and may be generally referred to as hidden lingual mechanisms.

BRIEF DESCRIPTION OF THE DRAWINGS

A clearer understanding of the invention will be had with reference to the following descriptions and drawings wherein:

FIG. 3 is a perspective exploded view showing a tubular member and a pair of insert members forming the dental appliance of the present invention;

FIG. 4 is a cross-sectional view of the dental appliance of the FIG. 3 with inserts located within the tubular member;

FIG. 5 is a perspective view of the dental appliance of the FIGS. 3 and 4 showing a round wire member held in position;

FIG. 6 is a side view of FIG. 5;

FIG. 7 is a cross-sectional view of the structure of FIG. 5 taken along line 7—7 of FIG. 5;

FIG. 8 is a perspective view of another embodiment of the dental appliance of the present invention including a metal tubular member and a single insert for supporting an elongated tube;

FIG. 9 is a cross-sectional view of the structure of FIG. 8 taken along lines 9—9 of FIG. 8;

FIG. 10 is a perspective view of a pair of wire members maintained in spaced relationship by clip members forming another part of the present invention;

FIG. 11 is an enlarged perspective view of one of the clip members of FIG. 10;

FIGS. 12 and 13 illustrate two alternative embodiments of the clip member of FIG. 10;

FIG. 14 is a perspective view of two wire members shown in FIG. 10 and supported in the dental appliance of the present invention shown in FIGS. 8 and 9;

FIG. 15 is a cross-sectional view of the structure of FIG. 14 taken along lines 15—15 of FIG. 14;

FIG. 16 is a cross-sectional view of one embodiment of the dental appliance of the present invention such as the dental appliance shown in FIGS. 3 and 4 and supporting a rectangular wire member having a vertical axis; and FIG. 17 is a cross-sectional view of one embodiment of the dental appliance of the present invention, as shown in FIGS. 3 and 4, and supporting a rectangular wire having a horizontal axis.

DESCRIPTION OF THE PREFERRED EMBODIMENTS

Figure 1:
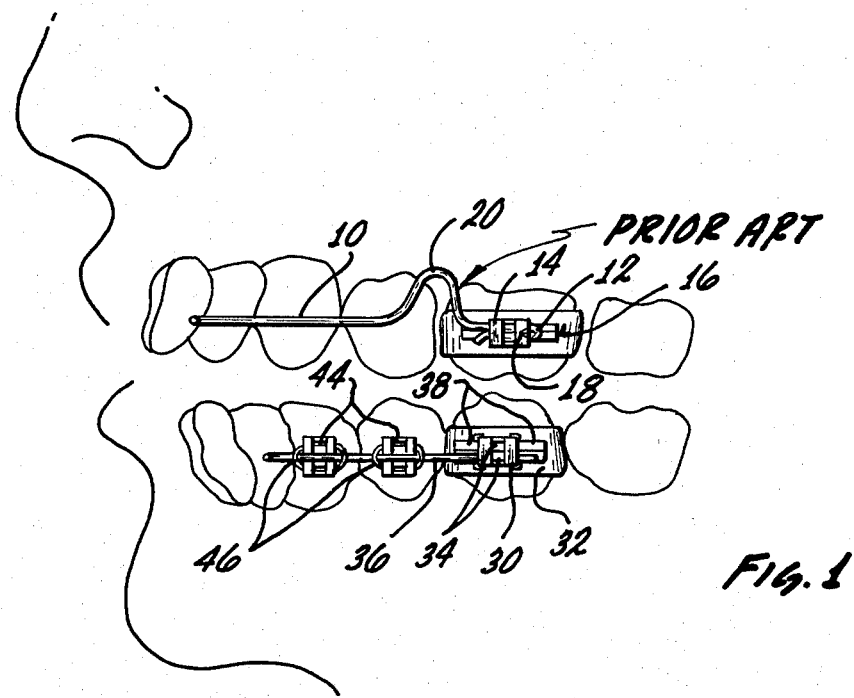
FIG. 1 illustrates upper and lower sets of teeth and with the upper set including a prior art dental mechanism and with the lower set including a dental mechanism incorporating a dental appliance of the present invention.

In FIG. 1 a side view of the upper and lower sets of teeth are shown in their relative position in the mouth. The upper set of teeth actually includes a prior art device, a portion of which may be incorporated as part of the dental appliance of the present invention. In particular, the prior art device shown positioned inside the upper set of teeth has been used only as an auxiliary structure in combination with outside mechanisms and has not been used to provide for the complete brace mechanism by itself.

In the prior art device, a heavy wire 10 is folded over at an end position 12 and is slid into and through the passage in a metallic tubular member 14. The tubular member 14 may be welded in an appropriate fashion to a band 16 and with the band maintained in position around the tooth using a standard dental cement. The end portion 12 of the heavy wire 10 may be locked in position within the tubular member 14 by the use of a crimp 18. The heavy wire 10 may include a loop portion 20 so that the overall length of the wire 10 may be adjusted. The prior art device is shown attached on the inside surface of the upper set of teeth. However, this prior art device has been very limited in use and, as indicated above, has only served as an auxiliary device in conjunction with more extensive outside mechanisms.

The lower set of teeth shown in FIG. 1 incorporates the use of a metallic tubular member 30 similar to the tubular member 14 of the prior art. The tubular member 30 is welded to a band 32 and with the band maintained in position around the tooth using standard dental cement. In the lower structure shown in FIG. 1 forming one embodiment of the dental appliance of the present invention, the metallic tubular member 30 receives at least one and, in the specific example shown in FIG. 1, a pair of lingual sheath inserts 34 which individually act either as a spacer or reducer or combination of both. This may all be seen more clearly with reference to FIGS. 3 through 7. FIGS. 3 and 4 show in general the combination of the metallic tubular member 30 plus the pair of inserts 34. The inserts 34 are identical to each other and are oriented 180° to each other to completely fill-in the passage within the metallic tubular member 30 and to provide two smaller passages through the tubular member 30.

As can be seen in FIGS. 5 through 7, the upper insert 34 serves as a spacer while the lower insert 34 additionally serves as a reducer to receive a thin wire 36. In the one embodiment of the dental appliance of the present invention as shown in FIGS. 3 through 7, the combination of the metallic tubular member 30 and the pair of inserts 34 may receive and support one or more wire-like members in passages each having cross-sections less than one half on the cross-section of the passage through the tubular member 30.

Each insert 34 has a width approximately equal to the width of the passage through the tubular member 30. In addition, each insert has a height approximately equal to one half of the height of the passage through the tubular member 30. As shown in FIGS. 3, 5 and 6, the metallic tubular member 30 includes wing portions 38 to give a broader base portion for welding to the band member 32 shown in FIG. 1. In order to lock the inserts 34 within the tube, each insert is formed as a U-shaped member composed of a soft metal and having extending arms 40. These are seen clearly in FIG. 3. Each insert 34 may be slipped into the passage through the metallic tubular member 30 and with the arms 40 bent over to lock the insert in position within the tubular member 30. This may be seen clearly in FIGS. 5 and 6.

FIGS. 5 through 7 thereby show the tubular member 30 receiving two of the inserts 34 and with each insert locked in position. Also, as indicated above, the upper insert serves as a spacer whereas the lower insert 34 additionally serves as a reducer so as to provide a passage with a smaller cross-section so as to receive the smaller wire 36. The wire may be held in position by the use of a right-angle turn, as shown at position 42 in FIG. 5.

FIG. 1 shows the use of the dental appliance of the present invention in combination with the thin wire 36 on the lower set of teeth so as to provide for a complete mechanism to reposition the teeth and correct irregularities. The thin wire 36 is used to apply the proper pressure and direction of force on individual bracket members 44 which bracket members are cemented onto the inside surfaces of the particular ones of the teeth which need to be corrected. The thin wire 36 is held in position against the bracket member using individual O-ring members 46 which are received in recessed portions of the bracket members 44 and pass over and hold the wire member 36. It is to be appreciated that other structures for holding the wire 36 against the brackets 44 may be used.

The force applied by the wire member against individual bracket members 44, supply individual pressure to individual teeth. Each bracket member 44 spreads the pressure on the tooth and by the appropriate location of the bracket member on the inside surface of the tooth, a specific directional force on the tooth may be applied to pull, push, rotate, or torque the tooth to the proper position. The bracket members 44 may be bonded onto the inside surface of the teeth using a very strong adhesive such as an adhesive sold by 3M and designated by the trade name Concise and which in general is an acrylic modified epoxy resin.

Figure 2:
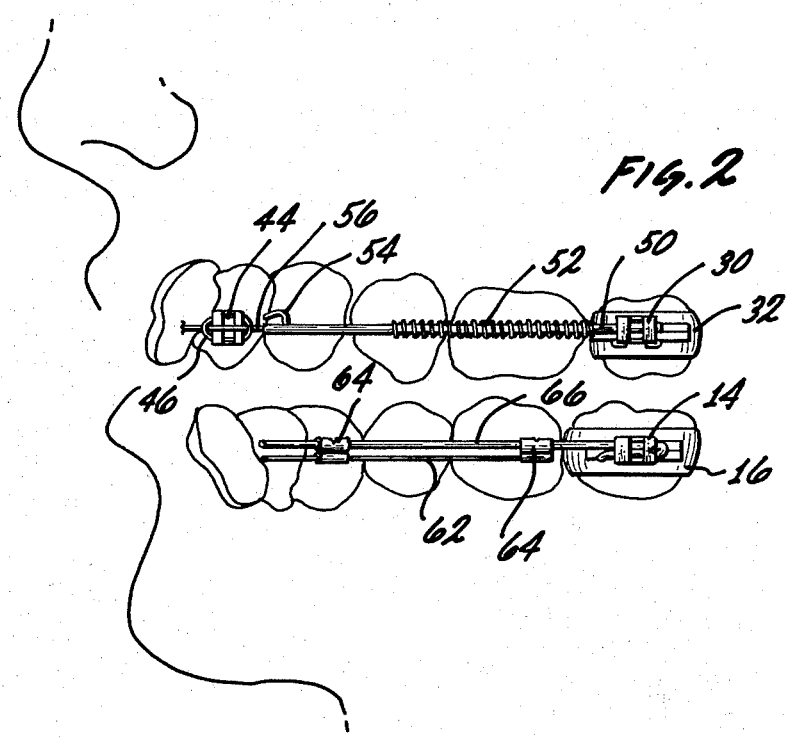
FIG. 2 illustrates upper and lower sets of teeth and with the upper set showing a dental mechanism incorporating a dental appliance of the present invention and with the lower structure showing a clip appliance of the present invention.

FIG. 2 illustrates the upper and lower sets of teeth incorporating a dental appliance and a clip both constructed in accordance with the teachings of the present invention. In particular, the upper set of teeth shown in FIG. 2 includes the metallic tubular member 30 welded onto a band 32 and with the band maintained in position around the tooth using the standard dental cement. An elongated tube 50 passes through and is maintained in position within a passage in the metallic tubular member 30. This may be seen more clearly with reference to FIGS. 8 and 9. As can be seen in FIGS. 8 and 9, the tubular member 30 receives the single insert 34 at the lower position, although it is appreciated that the insert 34 could be located at the upper position. The insert 34 in FIGS. 8 and 9 serves as a spacer thereby allowing the tubular member 30 to receive the elongated tube 50 and to maintain and properly locate the tube 50.

The elongated tube 50 forms a relatively rigid structure and the tube 50 may support either a coiled spring 52 or a hook member 54 or both. The tube 50 my extend only partially around the inside surface of the teeth and with the anterior end of the tube 50 receiving and supporting a thin wire member 56. The wire 56 extends from the end of the tube 50 and may be locked in position such as by crimping or welding the wire 56 within the end of the tube 50. The thin wire member 56 may continue around the inside surface of the front teeth and with a complimentary structure on the other side of the mouth. The thin wire member 56 may be received within brackets 44 attached to the teeth in a similar fashion as shown and described with reference to FIG. 1.

The spring 52 or the hook 54 may be used to provide for either a forward or backward pressure by the combination of the tubular member 50 and the thin wire member 56. This may be accomplished in the following manner. A force may be provided in a backward direction by looping a resilient member such as an elastic band around the hook 54 and around the rearward end of the tubular member 30 or the tube 50. A force may be provided in a forward direction by compressing the spring member 52 from the front toward the rear and then crimping the metallic tube 50 of the front end of the compressed spring and which expands the tube 50 to a greater diameter so that the compressed spring will tend to push the metal tube 50 and the thin wire 56 in a forward direction. It can be seen, therefore, that various directions of force may be provided using the dental appliance of the present invention.

The dental appliance of the present invention previously described may be used in conjunction with another device of the present invention which device forms a clip member to support both a larger and smaller wire members. This clip member may be seen with reference to FIGS. 10 through 13 and with the end portions of the wires supported in the dental appliance of the present invention as shown in FIGS. 14 and 15. The end portion of one of the wires may also be supported in the prior art structure as shown in the lower portion of FIG. 2.

FIG. 10 illustrates a pair of wires 60 and 62 and with the upper wire 60 being larger in diameter than the lower wire 62. In order to maintain the wires 60 and 62 in the proper spatial relationship, a clip member 64 forming another device of the present invention is used. As shown in FIG. 10, a plurality of clip members 64 may be used at spaced locations. FIGS. 12 and 13 show alternate embodiments for the clip member 64 and with the clip member of FIG. 12 including a bottom tubular portion 66 forming a small opening and a larger split tubular portion 68 forming a larger opening. In FIG. 13, the clip member is formed by a unitary piece 70 having a figure eight configuration and preformed with a pair of openings and with a split at the larger opening.

In general, the thin wire 62 would be inserted into the smaller opening shown in both FIGS. 12 and 13 and with the larger wire 60 then inserted into position within the larger opening of the clip member. The clip member may be composed of a soft metal and would then be squeezed to the closed position as shown in FIG. 11, and with crimps 72 and 74 used to lock the wires in position. As shown in FIG. 2, the smaller wire 62 may be terminated within the rearward one of the clip 64 and with the larger wire continued and folded over to be received within the tubular member 14 in a smaller fashion to that shown and described with reference to the upper set of teeth of FIG. 1.

Alternatively, the ends of the wires 60 and 62 may be continued through the rearward clips 64 and may be held in position using the dental appliance of the present invention as shown in FIGS. 14 and 15. In FIGS. 14 and 15, it can be seen that the dental appliance includes the tubular member 30 and a single insert 34 which insert serves a double function of both a spacer and a reducer. The insert 34 serves as a spacer for the larger wire 60 and a reducer to receive the smaller wire 62. The ends of the wires 60 and 62 may be bent at right angles as shown at positions 76 and 78 so as to lock the ends of the wires within the tubular member 30. The clip 64, therefore, may serve the function of maintaining and properly locating a pair of different size wires and with the ends of these wires then held properly in position using the dental appliance including the tubular member 30 and the single insert 34.

FIGS. 16 and 17 illustrate yet another use of the dental appliance of the present invention including the metallic tubular member 30 and inserts 34. In FIG. 16, a pair of inserts is used and with the upper insert serving as a spacer and with the lower insert serving as a reducer to receive a wire 80 having a rectangular configuration along a vertical axis. In FIG. 17, the metallic tubular member 30 is also used with a pair of inserts 34 and with upper insert serving as a spacer and with the lower insert serving as a reducer to receive a rectangular metal wire 82 having a horizontal axis. The use of these rectangular wires may be desirable to provide different types of pressures in the lingual mechanisms which may be accomplished with the dental appliances of the present invention.

It is to be appreciated that at times when the inserts 34 have been shown in either an upper or lower position, the positions may be reversed. It is also to be appreciated that at times when a pair of inserts have been shown wherein one insert has served as a spacer and the other as a reducer it may be possible to use only a single insert and with a larger size wire used. For example, in FIGS. 16 and 17, only a single spacer insert may be used and with larger size wires 80 and 82 used in the remaining space. It is also to be appreciated that the dental appliance of the present invention may provide for any of two wires of the above described shapes and sizes.

Finally, it is to be appreciated that the present application has been shown with reference to particular embodiments but that various other adaptations and modifications may be made so that the present invention is only to be limited by the appended claims.

I claim:

1. A dental appliance for the attachment to a band which band encircles a tooth and for use in supporting a variety of different sizes and shapes of elongated wire-like members including:

a metal tubular member and with the metal tubular member having an open passage extending from one end of the tubular metal to the other end and with the passage having a symmetrical cross-section and a greater height than width and with the passage having top and bottom portions each large enough to receive different sizes and shapes of wire-like members, at least one insert member positioned within the passage through the tubular member at either the top or bottom portion and having a diameter in one direction approximately the same as the inside width of the passage and having a dimension in the other direction substantially equal to one-half of the height of the pressure through the tubular member and with two inserts substantially filling the passage, the insert member also having an elongated passage smaller in cross-section than one-half of the passage through the tubular member and with the use of one or two inserts providing for a variety of different size passages through the tubular member for receiving and supporting a variety of different sizes and shapes of elongated wire-like members, and means for removability maintaining the at least one insert member in position within the tubular member.

2. The dental appliance of claim 1 wherein one insert is positioned within the tubular member so that the dental appliance may receive and support wire-like members of a smaller size within the passage through the one insert and/or may receive and support wire-like members of a larger size within the remaining portion of the passage through the tubular member.

3. The dental appliance of claim 1 wherein two inserts are positioned within the tubular member so that the dental appliance may receive and support wire-like members of a smaller size within the passages through either one or both the inserts.

4. The dental appliance of claim 1 wherein one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member.

5. A dental applicant for the attachment to a band which band encircles a tooth and for use in supporting a variety of different sizes and shapes of elongated wire-like members including:
a metal tubular member and with the metal tubular member having an open passage extending from one end of the tubular metal to the other end and with the passage having a symmetrical cross-section and a greater height than width and with the passage having top and bottom portions each large enough to receive different sizes and shapes of wire-like members,
at least one removable insert member positioned within the passage through the tubular member at either the top or bottom portion and having a diameter in one direction approximately the same as the inside width of the passage and having a dimension in the other direction substantially less than the height of the passage through the tubular member and with a plurality of inserts substantially filling the passage, and
the insert member also having an elongated passage smaller in cross-section than the cross-section of the passage through the tubular member and with the use of one or a plurality of inserts providing for a variety of different size passages through the tubular member for receiving and supporting a variety of different sizes and shapes of elongated wire-like members.

6. The dental appliance of claim 5 wherein one insert is positioned within the tubular member so that the dental appliance may receive and support wire-like members of a smaller size within the passage through the one insert and/or may receive and support wire-like members of a larger size within the remaining portion of the passage through the tubular member.

7. The dental appliance of claim 5 wherein a plurality of inserts are positioned within the tubular member so that the dental appliance may receive and support wire-like members of a smaller size within the passages through either one or the plurality of the inserts.

8. The dental appliance of claim 5 wherein one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member.

9. A dental appliance for the attachment to a band which band encircles a tooth and for use in supporting a variety of different sizes and shapes of elongated wire-like members including:
a metal tubular member and with the metal tubular member having an open passage extending from one end of the tubular metal to the other end and with the passage having a greater height than width and with the passage large enough to receive different sizes and shapes of wire-like members,
at least one insert member positioned within the passage through the tubular member and having a diameter in one direction approximately the same as the inside width of the passage and having a dimension in the other direction substantially equal to one-half of the height of the passage through the tubular member and with two inserts substantially filling the passage,
the insert member also having an elongated passage smaller in cross-section than one-half of the passage through the tubular member and with the use of one or two inserts providing for a variety of different size passages through the tubular member for receiving and supporting a variety of different sizes and shapes of elongated wire-like members,
means for maintaining the at least one insert member in position within the tubular member wherein the one insert is positioned within the tubular member so that the dental appliances receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member, and
the at least one clip member has an open position and a closed position and with the clip member in the open position having at least one of the openings larger in size than the size of the opening in the closed position and with the clip member composed of soft metal so that the clip member may be squeezed together from the open position to the closed position.

10. A dental appliance for the attachment to a band which band encircles a tooth and for use in supporting a variety of different sizes and shapes of elongated wire-like members including:
a metal tubular member and with the metal tubular member having an open passage extending from one end of the tubular metal to the other end and with the passage having a greater height than width and with the passage large enough to receive different sizes and shapes of wire-like members,
at least one insert member positioned within the passage through the tubular member and having a diameter in one direction approximately the same as the inside width of the passage and having a dimension in the other direction substantially equal to one-half of the height of the passage through the tubular member and with two inserts substantially filling the passage,
the insert member also having an elongated passage smaller in cross-section than one-half of the passage through the tubular member and with the use of one or two inserts providing for a variety of different size passages through the tubular member for receiving and supporting a variety of different sizes and shapes of elongated wire-like members, means for maintaining the at least one insert member in position within the tubular member wherein the one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member, and the at least one clip member is formed as a pair of joined cylinders and with at least one of the cylinders split along its length and with the wire-like member received within the one cylinder and the one cylinder squeezed together to close the split to support the wire-like member.

11. A dental appliance for the attachment to a band which band encircles a tooth and for use in supporting a variety of different sizes and shapes of elongated wire-like members including:

a metal tubular member and with metal tubular member having an open passage extending from one end of the tubular metal to the other end and with the passage having a greater height than width and with the passage large enough to receive different sizes and shapes of wire-like members, at least one insert member positioned within the passage through the tubular member and having a diameter in one direction approximately the same as the inside width of the passage and having a dimension in the other direction substantially equal to one-half of the height of the passage through the tubular member and with two inserts substantially filling the passage, the insert member also having an elongated passage smaller in cross-section than one-half of the passage through the tubular member and with the use of one or two inserts providing for a variety of different size passages through the tubular member for receiving and supporting a variety of different sizes and shapes of elongated wire-like members, and means for maintaining the at least one insert member in position within the tubular member wherein the one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member and the at least one clip member is formed as a unitary piece having a figure eight configuration and split along its length and with the unitary piece squeezed together to close the split to support the wire-like members.

12. A dental appliance for the attachment to a band which band encircles a tooth and for use in supporting a variety of different sizes and shapes of elongated wire-like members including:

a metal tubular member and with the metal tubular member having an open passage extending from one end of the tubular metal to the other end and with the passage having a greater height than width and with the passage large enough to receive different sizes and shapes of wire-like members, at least one insert member positioned within the passage through the tubular member and having a diameter in one direction approximately the same as the inside width of the passage and having a dimension in the other direction substantially less than the height of the passage through the tubular member and with a plurality of inserts substantially filling the passage, the insert member also having an elongated passage smaller in cross-section than the cross-section of the passage through the tubular member and with the use of one or a plurality of inserts providing for a variety of different size passages through the tubular member for receiving and supporting a variety of different sizes and shapes of elongated wire-like members and wherein the one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member, and the at least one clip member has an open position and a closed position and with the clip member in the open position having at least one of the openings larger in size than the size of the opening in the closed position and with the clip member composed of soft metal so that the clip member may be squeezed together from the open position to the closed position.

13. A dental appliance for the attachment to a band which band encircles a tooth and for use in supporting a variety of different sizes and shapes of elongated wire-like members including:

a metal tubular member and with the metal tubular member having an open passage extending from one end of the tubular metal to the other end and with the passage having a greater height than width and with the passage large enough to receive different sizes and shapes of wire-like members, at least one insert member positioned within the passage through the tubular member and having a diameter in one direction approximately the same as the inside width of the passage and having a dimension in the other direction substantially less than the height of the passage through the tubular member and with a plurality of inserts substantially filling the passage, the insert member also having an elongated passage smaller in cross-section than the cross-section of the passage through the tubular member and with the use of one or a plurality of inserts providing for a variety of different size passages through the tubular member for receiving and supporting a variety of different sizes and shapes of elongated wire-like members and wherein the one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member, and wherein the at least one clip member is formed as a pair of joined cylinders and with at least one of the cylinders split along its length and with the wire-like member received within the one cylinder and the one cylinder squeezed together to close the split to support the wire-like member.

14. A dental appliance for the attachment to a band which band encircles a tooth and for use in supporting a variety of different sizes and shapes of elongated wire-like members including:

a metal tubular member and with the metal tubular member having an open passage extending from one end of the tubular metal to the other end and with the passage having a greater height than width and with the passage large enough to receive different sizes and shapes of wire-like members, at least one insert member positioned within the passage through the tubular member and having a diameter in one direction approximately the same as the inside width of the passage and having a dimension in the other direction substantially less than the height of the passage through the tubular member and with a plurality of inserts substantially filling the passage, the insert member also having an elongated passage smaller in cross-section than the cross-section of the passage through the tubular member and with the use of one or a plurality of inserts providing for a variety of different size passages through the tubular member for receiving and supporting a variety of different sizes and shapes of elongated wire-like members and wherein one insert is positioned within the tubular member so that the dental appliance receives and supports a smaller wire-like member within the passage through the one insert and receives and supports a larger wire-like member within the remaining portion of the passage through the tubular member and additionally including at least one clip member having a pair of different size openings and with a first opening of the pair of a size to receive and support the smaller wire-like member and with a second opening of the pair of a size to receive and support the larger wire-like member, and wherein the at least one clip member is formed as a unitary piece having a figure eight configuration and split along its length and with the unitary piece squeezed together to close the split to support the wire-like members.

* * * * *